United States Patent
Suri et al.

(10) Patent No.: US 6,664,236 B2
(45) Date of Patent: Dec. 16, 2003

(54) **SYNERGISTIC COMPOSITION OF BIOACTIVE FRACTION ISOLATED FROM *BARLERIA PRIONITIS LINN* AND A METHOD OF TREATMENT FOR HEPATOTOXICITY, IMMUNO-DEFICIENCY AND FATIGUE AND A PROCESS THEREOF**

(75) Inventors: J. L. Suri, Jammu (IN); S. K. Banerjee, Jammu (IN); Subhash Chandra Taneja, Jammu (IN); A. S. Anand, Jammu (IN); Anil Prabhakar, Jammu (IN); Bupinder Singh Jaggi, Jammu (IN); A. K. Saxena, Jammu (IN); Bal Krishan Chandan, Jammu (IN); Sukhdev Swami Handa, Jammu (IN)

(73) Assignee: Council of Scientific and Industrial Research, New Delphi (IN)

( * ) Notice: Subject to any disclaimer, the term of this patent is extended or adjusted under 35 U.S.C. 154(b) by 0 days.

(21) Appl. No.: 10/100,166

(22) Filed: Mar. 19, 2002

(65) Prior Publication Data

US 2003/0181397 A1 Sep. 25, 2003

(51) Int. Cl.$^7$ .................. A01N 65/00; A61K 35/78; A61K 31/7048

(52) U.S. Cl. ........................................ 514/27; 424/725
(58) Field of Search ............................ 514/27; 424/725

(56) References Cited

PUBLICATIONS

Damtoft et al., "Structural Revsion of Barlerin and Acetyl Barlerin," *Tetrahedron Letters* (1982), vol. 23, No. 40, pp. 4155–4156, Pergamon Press Ltd., Great Britain.

Taneja et al., "Structures of Two New Iridoids From *Barleria Prionitis*Linn," *Tetrahedron Letters* (1975), No. 24, pp. 1995–1998, Pergamon Press, Great Britain.

Harborne, "Angiospermae Dicotyledonae," *Phytochemistry* (1971), vol. 10, pp. 2822–2823, Pergamon Press, England.

*Primary Examiner*—Herbert J. Lilling
(74) *Attorney, Agent, or Firm*—Foley & Lardner

(57) ABSTRACT

The present invention provides a synergistic composition of bioactive fraction essentially constituting iridoid glucosides, acetyl barlerin and shanzhiside methyl ester isolated from a plant source *Barleria prionitis linn* along with a process for the isolation of the bioactive fraction, the present invention also relates to a method of treating mammals and humans for hepatotoxicity, stress and immuno-deficiency with the synergistic bioactive composition.

62 Claims, No Drawings

SYNERGISTIC COMPOSITION OF BIOACTIVE FRACTION ISOLATED FROM *BARLERIA PRIONITIS LINN* AND A METHOD OF TREATMENT FOR HEPATOTOXICITY, IMMUNO-DEFICIENCY AND FATIGUE AND A PROCESS THEREOF

FIELD OF INVENTION

The present invention relates to a synergistic composition of bioactive constituent essentially constituting iridoid glucosides, acetyl barlerin and shanzhiside methyl ester isolated from a plant source *Barleria prionitis linn* along with a process for the isolation of the bioactive fraction. The present invention also relates to a method of treating mammals and humans for hepatotoxicity, stress and immuno-deficiency with the synergistic bioactive composition.

BACK GROUND AND PRIOR ART REFERENCES

*Barleria prionitis Linn.* (Family: Acanthaceae) is a well-known plant used in the indigenous system of medicine in India. Almost all its parts are used as medicine. The leaves are diuretic and are used in urinary infections and for the treatment of paralytic stroke, rheumatic pains and stomach disorders. The plant has antiseptic properties and its decoction is used as a wash in dropsy. The roots are used for toothache and for inflammatory disorders. The bark is given in whooping cough and as an expectorant [L. V. Asolkar et al; Glossary of Indian Medicinal Plants (second supplement), Council for Scientific and Industrial Research (CSIR), New Delhi, 1992, p. 115; Wealth of India: Raw Materials, CSIR, New Delhi, 1988, Vol. 11 B, p. 47].

The first report on chemical investigation of this plant appeared in 1970 when Moitra et al. reported the presence of β-sitosterol [Moitra, S. K. et al. (*Bull. Calcutta Sch. Trop. Med*; 1970, 18,7]. Harborne et al. reported the isolation of scutellarein-7-rhamnosyl glucoside from fresh flowers [Harborne, J. B. et al; *phytochemistry*, 1971, 10, 2822]. The structure of this compound is later modified as 5,6,4'-trihydroxy-7-0-neohesperidosylflavone [Nair, A. G. Ramchandran et al., *Ind. J.Chem.* 1982, 21 B, 1135].

The leaves and stems showed the presence of five iridoid glucosides. Four of them, acetylbarlerin (6,8-di-O-acetyl shanzhiside methyl ester), barlerin (8-O-acetyl shanzhiside methyl ester), shanzhiside methyl ester and 6-0-acetyl shanzhiside methyl ester have been characterized [Taneja, S. C. and Tiwari, H. P., *Tetrahedron Lett*, 1975, 1995; Damtoft, S. et al., *ibid*, 1982, 23,4155; Emary, N. A. et al. *Bull Pharm. Sci. Assuit Univ.* 1990, 13 (1), 65–72].

In view of the strong hepatoprotective and immunorestorative activities exhibited by the iridoid glucosides of the roots of *Picrorhiza kurroa* viz. kutkin, picroside and kutkoside [Ansari, R. A. et al. *Indian J. Med. Research*, 1988, 87,401; Sharma, M. L., Ph.D thesis entitled "Evaluation of immunomodulatory activity of some medicinal plants in mammals", 1991, University of Jammu] and *Vitex negundo* viz. agnuside and negundosides [Suri, J. L. et al., Indian Patent No. 178389/1997; Banerjee, S. K. et al. Indian Patent application No.1 16/DEL/98].

A detailed chemical and pharmacological investigation of *Barleria prionitis* (aerial parts) has led to the isolation of a bioactive fraction in about 14% yield having marked hepatoprotective, immunorestorative and antistress activities.

OBJECTS OF THE INVENTION

The main object of the present invention is to provide a synergistic composition of bioactive fraction essentially constituting iridoid glucosides, acetyl barlerin and shanzhiside methyl ester isolated from a plant source *Barleria prionitis linn*. Another object of the present invention is to provide a process for the isolation of the bioactive fraction. Yet another object of the present invention is to provide a method of treating mammals and humans for hepatotoxicity, stress and immuno-deficiency with the synergistic bioactive composition.

SUMMARY OF THE INVENTION

The present invention relates to a synergistic composition of bioactive fraction essentially constituting iridoid glucosides, acetyl barlerin and shanzhiside methyl ester isolated from a plant source *Barleria prionitis linn*. The present invention also provides a process for the isolation of the bioactive fraction. The present invention further provides a method of treating mammals and humans for hepatotoxicity, stress and immuno-deficiency with the synergistic bioactive composition.

DETAILED DESCRIPTION OF THE INVENTION

Accordingly, the present invention provides a novel synergistic pharmaceutical composition comprising a bioactive fraction of iridoid glucosides obtained from the plant *Barleria prionitis linn*, said bioactive fraction comprising the following ingredients (a) barlerin in the range of 1.6–6.2%;

(b) acetyl barlerin in the range of 0.015–0.38%;

(c) shanshizide methylesters in the range of 4.4–8.0%; and (d) pharmaceutically accepted additives, and having hepatoprotective, antistress and immunorestorative properties on subjects.

An embodiment of the present invention, wherein said composition is used to treat hepatic injury caused by Carbon tetrachloride, Acetaminophen, and Galactosamine.

Yet another embodiment of the present invention, wherein the preferred dosage for $CCl_4$ induced hepatotoxicity in mammals is 20–200 mg/kg of body weight.

Still another embodiment of the present invention, wherein the hepatoprotective activity in $CCl_4$ induced hepatotoxic mammals is upto 88%.

Yet another embodiment of the present invention, wherein the dosage for Acetaminophen induced hepatotoxicity in mammals is in the range of 50–100 mg/kg of body weight.

Still another embodiment of the present invention, wherein the hepatoprotective activity in acetaminophen induced hepatotoxicity in mammals is upto 86%.

Yet an other embodiment of the present invention, wherein the dosage for Galactosamine induced hepatotoxicity in mammals is in the range of 50–100 mg/kg of body weight.

Still another embodiment of the present invention, wherein the hepatoprotective activity in Galactosamine induced hepatotoxicity in mammals is upto 86%.

Yet another embodiment of the present invention, wherein the dosage for anti-fatigue activity in mammals is in the range of 25–100 mg/kg of body weight.

Still another embodiment of the present invention, wherein the preferred dosage for anti-fatigue activity in mammals is in the range of 50–100 mg/kg of body weight.

Yet another embodiment of the present invention, wherein the anti-fatigue effect in mammals is over 80%.

Still another embodiment of the present invention, wherein the dosage for immunorestorative activity is in the range of 50–100 mg/kg of body weight.

Yet another embodiment of the present invention, wherein the immunorestorative activity is up to 70%.

Still another embodiment of the present invention, wherein said composition reduces the elevated levels of serum glutamin-pyruvic transaminase (GPT) by about 92%.

Yet another embodiment of the present invention, wherein said composition reduces the elevated levels of serum glutamic-oxalo acetic transaminase (GOT) by about 74%.

Still another embodiment of the present invention, wherein said composition reduces the elevated levels of serum alkaline phosphatase (ALP) by about 88%.

Yet another embodiment of the present invention, wherein said composition reduces the elevated levels of serum triglycerides by about 88%.

Still another embodiment of the present invention, wherein the hepatoprotective activity of said composition against the elevated level of bilirubin is about 85.96%.

Yet another embodiment of the present invention, wherein the subject is selected from mammals and humans.

Still another embodiment of the present invention, wherein said composition is used singly or in combination with pharmaceutically acceptable carriers.

Yet another embodiment of the present invention, wherein said composition is administered to a subject in combination with a pharmaceutically acceptable additives, carriers, diluents, solvents, filters, lubricants, excipients, binder or stabilizers.

Still another embodiment of the present invention, wherein the desired dosage is administered for both preventive and curative properties.

Yet another embodiment of the present invention, wherein said composition is administered systemically, orally or by any clinically/medically accepted methods.

Still another embodiment of the present invention, wherein the subject is selected from animals, mammals, and preferably humans.

Still another embodiment of the present invention, wherein the preferred dosage for human beings is about 10–15 mg/kg of body weight.

The present invention further provides a process for the preparation of synergistic bioactive constituent comprising iridoid glucosides (a) acetyl barlerin (b) barlerin (c) shanzhiside methyl ester, said process comprising the steps of:

(a) extracting the powdered plant material with aqueous alcohol;

(b) concentrating the extract under reduced pressure at a temperature upto 45° C.;

(c) partitioning the concentrate between water and a moderately polar organic solvent; and (d) evaporating the aqueous constituent at a temperature upto 45° C. to complete dryness to yield the bioactive constituent.

An embodiment of the present invention provides, a process wherein the aqueous alcohol is selected from the group consisting of ethanol, methanol and a mixture thereof.

Yet another embodiment of the present invention provides, a process wherein the aqueous ethanol and aqueous methanol is in the range of 3:7 to 1:9.

Still another embodiment of the present invention provides, a process wherein the organic solvent used for partitioning is selected from the group consisting of chloroform, dichloromethene, diethyl ether, methylene chloride and/or ethyl acetate.

Yet another embodiment of the present invention provides, a process wherein the plant material is selected from the aerial parts consisting of leaves, stems and bark or mixture thereof.

Still another embodiment of the present invention, a process wherein the extract containing the bioactive constituent is either evaporated in a freeze drier or using a thin film evaporator.

The invention further provides a method of treating subjects with hepatotoxicity, immunodeficiency and stress, said method comprising administering a pharmaceutically effective dosage of synergistic composition of bioactive fraction comprising iridoid glucosides from the plant source extracted from *Barleria prionitis linn*, to the selected subjects, said composition comprising:

(a) barlerin 1.6–6.2%;

(b) acetyl barlerin 0.015–0.38%; and (c) shanshizide methylesters 4.4–8.0%.

Still another embodiment of the present invention provides, a method wherein said composition is used to treat hepatic injury caused by Carbon tetrachloride, Acetaminophen, and Galactosamine.

Yet another embodiment of the present invention provides, a method wherein the dosage for $CCl_4$ induced hepatotoxicity in mammals is in the range of 20–200 mg/kg of body weight.

Still another embodiment of the present invention provides, a method wherein the hepatoprotective activity in $CCl_4$ induced hepatotoxic mammals is upto 88%.

Yet another embodiment of the present invention provides, a method wherein the dosage for Acetaminophen induced hepatotoxicity in mammals is in the range of 50–100 mg/kg of body weight.

Still another embodiment of the present invention provides, a method wherein the hepatoprotective activity in acetaminophen induced hepatotoxicity in mammals is upto 86%.

Yet another embodiment of the present invention provides, a method wherein the dosage for Galactosamine induced hepatotoxicity in mammals is in the range of 50–100 mg/kg of body weight.

Still another embodiment of the present invention provides, a method wherein the hepatoprotective activity in Galactosamine induced hepatotoxicity in mammals is upto 86%.

Yet another embodiment of the present invention provides, a method wherein the dosage for anti-fatigue activity in mammals is in the range of 50–100 mg/kg of body weight.

Still another embodiment of the present invention provides, a method wherein the anti-fatigue effect in mammals is over 80%.

Yet another embodiment of the present invention provides, a method wherein the dosage for immunorestorative activity is in the range of 50–100 mg/kg of body weight.

Still another embodiment of the present invention provides, a method wherein the immunorestorative activity is upto 70%.

Yet another embodiment of the present invention provides, a method wherein said composition reduces the elevated levels of serum glutamin-pyruvic transaminase (GPT) by about 92%.

Still another embodiment of the present invention provides, a method wherein said composition reduces the elevated levels of serum glutamic-oxalo acetic transaminase (GOT) by about 74%.

Yet another embodiment of the present invention provides, a method wherein said composition reduces the elevated levels of serum alkaline phosphatase (ALP) by about 88%.

Still another embodiment of the present invention provides, a method wherein said composition reduces the elevated levels of serum triglycerides by about 88%.

Yet another embodiment of the present invention provides, a method wherein the hepatoprotective activity of said composition against the elevated level of bilirubin is about 85.96%.

Still another embodiment of the present invention provides, a method wherein the pathological condition is selected from stomach or liver disorder.

Yet another embodiment of the present invention provides, a method wherein the subject is selected from mammals and humans.

Still another embodiment of the present invention provides, a method wherein said composition is used singly or in combination with pharmaceutically acceptable carriers.

Yet another embodiment of the present invention provides, a method wherein said composition is administered to a subject in combination with a pharmaceutically acceptable additives, carriers, diluents, solvents, filters, lubricants, excipients, binder or stabilizers.

Still another embodiment of the present invention provides, a method wherein the desired dosage is administered for both preventive and curative properties.

Yet another embodiment of the present invention provides, a method wherein said composition is administered systemically, orally or by any clinically/medically accepted methods.

Still another embodiment of the present invention provides, a method wherein the subject is selected from animals, mammals, and preferably humans.

Yet another embodiment of the present invention provides, a method wherein the preferred dosage for human beings is about 10–15 mg/kg of body weight.

The invention is further explained in the form of following preferred embodiments and examples.

The bioactive fraction exhibits marked hepatoprotective, immunorestorative and antistress activities. A comparison with the known hepatoprotective agent silymarin on multi-dose treatment (p.o.) revealed that it is almost as effective as silymarin reducing the elevated levels of serum glutamin-pyruvic transaminase (GPT), glutamic oxalo acetic transaminase (GOT) and alkaline phosphatase (ALP) induced by paracetamol Similar effects are also observed with $CCl_4$ and galactosamine induced hepatic injury. In addition, to hepatoprotective activity the bioactive fraction showed marked antistress activity increasing the survival time under hypoxia and swimming survival time by 47.72% and 82% respectively following a two-week treatment at a dose of 100 mg/kg/day (p.o.).

It also showed marked immunorestorative activity stimulating both the cell mediated delayed type hypersensitivity (DTH) by 69.5% and humoral response (antibody titre) by 56.87% and immunorestorative activity in animals treated with cyclophosphamide, a known immunosuppressive chemotherapeutic agent by 33.3%.

The process of the present invention is illustrated by the following examples which are, however, not to be construed to limit the scope of the present invention.

EXAMPLE 1

The powdered aerial parts (leaves & stems) of *Barleria prionitis* (1 kg) are charged in a percolator, treated with 80% aqueous ethanol (4 liters) and left overnight at room temperature. The percolate is drained and the marc is extracted thrice each time with 3 liters of the solvent by keeping overnight at room temperature. The combined percolates are concentrated under reduced pressure in a thin film evaporator keeping the temperature of the bath below 45° C. The aqueous concentrate (500-ml) is extracted with ethyl acetate (4×250 ml). The combined ethyl acetate extracts are washed with 100 ml of water and washing is mixed with aqueous layer and evaporated under reduced pressure in a thin film evaporator below 45° C. to complete dryness; yield: 148 g. The product on HPLC analysis is found to contain acetyl-barlerin 0.37%, barlerin 6.12% and shanzhiside methyl ester 7.9%.

EXAMPLE 2

*Barleria prionitis* (aerial parts, 1 kg) is powdered and the material charged in a percolator. To this 4 liters of 80% aqueous methanol is added and the mixture allowed standing at room temperature overnight. The extract is drained and the marc further extracted thrice each time with 3 liters of the solvent by keeping overnight at room temperature. The pooled extracts are concentrated under reduced pressure below 45° C. to 500 ml. The aqueous concentrate is extracted with chloroform (4×250 ml). The combined chloroform extracts are washed with 100 ml. of water and the aqueous washing is mixed with the aqueous concentrate and evaporated to complete dryness in a thin film evaporator below 45° C., yield: 150 g. The product on HPLC analysis is found to contain acetylbarlerin 0.3%, barlerin 5.8% and shanzhiside methyl ester 7.5%.

EXAMPLE 3

The finely ground aerial parts (leaves and stems) of *Barleria prionitis* (1 kg) are charged in a percolator and extracted with 5 litres of 80% aqueous methanol by keeping overnight at room temperature. The process is repeated thrice with 3 litres each of aqueous methanol. The combined percolates are concentrated at 45° C. under reduced pressure (thin film evaporator) to 500 ml. The aqueous concentrate is extracted with ethyl acetate (4×250 ml). The combined organic extracts are washed with 100 ml of water and the aqueous washing is mixed with the aqueous concentrate and evaporated in a freezer drier to complete dryness; yield: 169 g: The product on HPLC analysis is found to contain 0.015% acetylbarlerin, 3.04% barlerin and 6.22% of shanzhiside methyl ester.

Hepatoprotective activity (H) is calculated by the following equation:

$$H=[1-(TC-V/VC-V)]\times100$$

Where TC, VC, and V are drug+toxin, vehicle+toxin and vehicle treated groups of animals respectively.

Human dose:

Doses for human being can be calculated by equivalent surface area doses conversion factor (equivalency on the basis of mg/sq. m.)

EXAMPLE 4

The pharmacological studies are conducted on Wistar albino rats (150–180 g) and Swiss albino mice (25–30 g) of either sex, colony—bred in the Institute's animal house. After procurement, all the animals are divided into different groups and left for one week for acclimatization to experimentation room and maintained on standard conditions (23±2° C., 60–70% relative humidity and 12 h, photo period). The animals are fed with standard rodents pellet diet and water ad libitum. There are six animals in each group except for general behavior and acute toxicity studies where ten animals are used in each group.

EXAMPLE 5

Hepatotoxins:

The hepatotoxin that causes acute hepatitis has close resemblance with the viral hepatitis, clinically, biochemically and histologically. Drugs are also causes of chronic hepatic disease as chronic hepatitis, fatty liver, cirrhosis and several vascular lesions of the liver. In many instances drug induced hepatitis proves indistinguishable from viral hepatitis. Chemically induced hepatic injury for experimental studies should be severe enough to cause cell death or to modify hepatic functions. The mechanism of acute hepatic injury depends upon the chemical compound and the species of animals used. Many chemicals produce parenchymal damage, arrest bile flow and cause jaundice (cholretic injury). The applicants have studied hepatoprotective activity against $CCl_4$, paracetamol, and D-galactosamine induced hepatotoxicity.

Carbon tetrachloride ($CCl_4$):

One of the most powerful hepatotoxins (in term of severity of injury). It causes toxic necrosis, which leads to biochemical changes having clinical features similar to those of acute viral hepatitis (Vogel, 1977, Bramanti et. al., 1978, Agarwal 1983, Kumar et. al., 1992). Liver injury is produced by administration of $CCl_4$ mixed with liquid paraffin. Animals are given single dose of $CCl_4$ (50 $\mu l.kg^{-1}$, p.o.) in acute single treatment and (0.5 $ml.kg^{-1}$, p.o.) in case of multitreatment with drug. It is administered orally (p.o.) by gastric intubation. The control animals received the equal volume of liquid paraffin. The data are recorded in Tables 3 & 4.

Paracetamol (APAP, acetaminophen):

It is a therapeutic agent widely used as analgesic/antipyretic drug. When taken in large doses it causes hepatic necrosis which leads to biochemical changes having clinical features similar to those of acute viral hepatitis in humans (Proudfoot and Wright, 1970). The similar effect is observed in animals (Potter et. al., 1973). The toxic effect can be potentiated if it is given several hours after the anesthetic ether inhalation (Wells et. al., 1985).

Liver injury is induced by injecting paracetamol (200 $mg.kg^{-1}$) interaperitoneally in normal saline (pH 9.4) six hour after inhalation of anesthetic ether (4ml/4min/6animals) in a closed chamber. The control animals received the equal volume of vehicle. (Table 2)

D-Galactosamine:

It is one of the toxins that induce hepatic inflammatory conditions in the rat liver that clinically resembles to viral hepatitis. The mechanism of GalN induced liver injury has been extensively examined and this model is now accepted as one of the authentic systems of liver damage (Bauer et. al., 1974, Al-Tuwaijiri et. al., 1981; Zimmerman, H. J. 1978). (Table1)

Hepatic damage is produced by injecting GalN (300 $mg.kg^{-1}$) subcutaneously in normal saline. The control animals received the equal volume of vehicle.

EXMAPLE 6

Treatment With bio-Active Compound and Silymarin:

Freshly prepared suspension (1 to 5%, w/v) in 0.2% gum acacia in normal saline is used for all the experiments except for toxicity studies where (10%, w/v) suspension is used. Silymarin (positive control and other reference drugs suspension (1 to 5%, w/v) in 0.2% gum acacia is used.

The following parameters are studied:

GPT and GOT: Pyruvate formed by transamination reaction is determined spectrophotometrically after reaction with 2,4-dinitrophenylhydrazine (Reitman and Frankel, 1957).

ALP: p-nitrophenol formed in alkaline medium is measured spectrophotometerically using p-nitrophenyl phosphate as substrate (Walter and Schutt, 1974).

Bilirubin: Total bilirubin is measured by diazotization reaction with $NaNO_2$ (Malloy and Evelyn, 1937)

Triglycerides: Triglycerides from serum are extracted with isopropanol and sopanified with KOH. The liberated glycerol is converted to formaldehyde by periodate and determined after reaction with acetyl acetone. Triolein is used as standard (Neri and Firings, 1973).

EXAMPLE 7

General Behaviour and Acute Toxicity:

Using different doses (10, 30, 100, 1200, 1400, 1600, 1800 and 2000 $mg.kg^{-1}$) of extract and TAF given orally to the groups of 10 mice for each dose, while one group with same number of mice served as control. The animals are observed continuously for 1 h and then half hourly for 4 h for any gross behavioral changes and general motor activity, writhing, convulsion, response to tail pinching, gnawing, piloerection, pupil size, fecal output, feeding behavior etc. and further up to 72 h for any mortality. Acute $LD_{50}$ values in mice are calculated by the method of Miller and Tainter, (1944). Mortality of animals in all the groups used in different models for determining hepatoprotective activity during the period of treatment is also recorded as a rough index of subacute toxicity.

Statistical analysis:

The data obtained are subjected to statistical analysis using ANOVA for comparing different groups (Armitage, 1987) and Dunnett's t test for control and test groups (Dunnett, 1964). The two tailed paired student t test for comparing means before and after treatment and one tailed unpaired student t test for comparing control and drug treated groups (Ghosh, 1984) are used. The p value of <0.05 or less is taken as the criterion of significance.

EXAMPLE 8

Immunomodulatory Activity

An adaptogen exert a strong immunomodulatory influence in the healthy test subjects and can be considered non-specific immunostimulants. Stress causes significant depression in the immunological functions (Solomon et al, 1985; Harman, D., 1993). Our studies showed that TAF during stress render vital support to the immune system (Table 14). This is further supported by its effect on carrageenan induced trauma in rats (Swingle, 1974; Bowen and fauci, 1984, Sternberg and Licinio, 1995.; Ottemess and Bliven, 1985;) Inhibition of trauma induced by Carrageenan may be achieved by stabilising the blood vessels membrane that stabiles the vascular permeability neutralizing the chemical mediators (Kumar et al, 1992) and stimulating the immune mediated responses, (humoral and cell mediated immunity) (Arrigoni-Martelli and Bramm. 1975 Arrigoni-Martelli et al 1976;) Immuno-stimulant activity is associated with the enhancement of primary & secondary anti body synthesis which is further supported by its effects in models of DTH using SRBC as antigen. (Arrigoni-Martelli et al, 1976) Table, FIG. 14)

Immuno-stimulant activity in normal mice

Eight groups of mice are used (Table 14). The mice are immunized (Sharma et al, 1996) by an intraperitoneal injection of fresh sheep erythrocytes (SRBC, washed in a large volume. of pyrogen free sterile normal saline) 0.2 ml of $5 \times 10^9$ SRBC/ml one hour after the drug treatment on day 0 and challenged by injecting the same amount of SRBC i.p. on day +7 after taking a small amount of blood from orbital sinus from all the animals and serum separated for primary antibody titer. On day +14 again blood collected 1 h after the last dose administered from all the animals for secondary antibody titer (Sharma et al, 1992) by the hemagglutination technique (Nelson and Mildenhall, 1967) using serial two fold dilution in 'V' bottomed 96 well microtiter plates. The highest dilution showing visible agglutination is taken as the antibody titer.

Immuno-stimulant activity in immunosuppressed mice

Eight groups of mice are used. "Cyclophosphamide" (CY) 250 mg $kg^{-1}$, p.o. is given for two days at the interval of 24 h except Group 1 and 3. On day 3rd all the animals are immunised[19] (Sharma et al, 1996) with SRBC (0.2 ml of $5 \times 10^9$ SRBC $ml^{-1}$ i.p.) one hour after the drug treatment. Different doses of the test drug dissolved in normal saline and the vehicle (normal saline) given orally (p.o.) once daily at the interval of 24 h from day 3rd to 7th) On day +7 blood collected 1 h after the last dose had been administered from all the animals for antibody titer (Sharma et al,1992) by the hemagglutination technique (Nelson and Mildenhall, 1967) The highest dilution showing visible agglutination is taken as the antibody titer.

Delayed type of hypersensitivity (DTH) reaction in mice

Mice are sensitized by injecting 20 µl. of $5 \times 10^9$ SRBC/ml subcutaneously (s.c.) into the right hind foot paw on day 0 and challenged by injecting the same dose of SRBC (i.d.) m into the left hind foot paw on day +7 (Doherry, 1981). The thickness of left hind foot pad mof each mouse is measured using a spheromicrometer (reading to 0.1 mm.) 24 h after the challenge and expressed as the mean ±S.E. for each group (Table 14).

Anti-hypoxia effect

The anti-hypoxia effect is related to improved or raised cerebral resistance to hypoxia and reduced cerebral consumption of oxygen in acute hypoxia (Qu et al., 1988). When mice are exposed to hypobaric environment for a specified period, mitochondria of heart and brain cells of mice are seriously damaged and brain neurotransmitters i.e. norepinephrine (NE), dopamine (DA), serotonin (5-HT) and acetylcholine (ACh) are significantly decreased. Our results demonstrated that TAF in graded doses of 12.5–100 mg.$kg^-$1, p.o. prolonged the hypoxia time in dose-related manner (Table 2). The effect is probably related to increase in the cerebral resistance to hypoxia and reducing cerebral consumption of oxygen in acute hypoxia. The protective action of BF on acute hypoxia mice may be due to the action of BF on pituitary-adrenal gland axis (Lu et al., 1988).

The manifestation of stress of any reason causes the deleterious changes and alters the normal functioning of the body, decreases labour efficiency, increases fatigue, reduces locomotor activity and induces mental depression. A true adaptogen is supposed to reverse such effects (Brekhman, 1965, Brekhman, 1969). The stress leads to central neuronal lesions (Anisman et al., 1985) since behavioural depression is a common consequence of stress (Solomon et al., 1985) and the anti-fatigue activity largely depends on the neurochemicals i.e. central NE and 5-HT. Our results show that pretreatment with BF increases the labour efficiency and decreases fatigue (Table 1).

EXPERIMENTAL MODELS

Hypoxia Time:

A set of six groups of mice is used. On day 15, one hour after the treatment, the hypoxia time (Caillard et al, 1975) is recorded individually of all the animals. The animal are placed in an empty glass jar of 300 ml capacity attached with electronic watch, the jars are made air tight with greased glass stopper and time till onset of convulsion is recorded (Table 13).

Swimming performance time:

A set of Seven groups of mice is used. On day 15, one hour after the treatment, swimming time (Porsolt et al., 1977) of all the animals is measured individually. The animals are allowed to swim inside a perpex glass beaker (30 cm high with 20 cm diameter containing water up to 25 cm height) maintained at 26±1° C. with a continuous air current from the bottom. The end point of swimming endurance is taken as when mice remained at the bottom for more then 10 seconds (Table 1).

Stress alters the normal functioning of the body (Brekhman, 1965). In a special contrivance when animal forced to swim, becomes immobile after an initial period of vigorous activity resembles a state of mental depression (Porsolt et al., 1977; Anisman et al., 1985), and causes sever fatigue. Our results showed that pretreatment with 'TAF' increase the labor efficiency and decrease fatigue, as documented by the increase of swimming performance and antifatigue activity perhaps by maintaining neuromuscular coordination (Anisman et al., 1985) (Table 13).

Antifatigue effect:

Mice are trained to stay on rotating rod. The mice, which stayed on rotating rod (UGO Basile, Italy) at 20 r.p.m. for more than 5 minutes in three successive trials for 5 consecutive days, are used in this study. On day 15, one hour after the treatment, animals of all the groups except control without stress are exhausted by swimming continuously for two hours. The animals are placed on the rotating rod immediately after drying with tissue paper to monitor the anti-fatigue (Dua et al., 1989) and motor coordination effect. The number of mice that stayed on the rotarod for 180 seconds or more are considered untired with full motor coordination. The percent effect of each group is calculated on the basis of number of mice that stayed on rotarod for >180 seconds by quantal response i.e. all or none response in a group. The same animals are again placed on rotarod after 30 minutes of removal from swimming bath to monitor the anti-fatigue effect once again. Similarly the animals of two groups which are not allowed to swim are also placed on rotating rod to monitor antifatigue effect (Table 13). Anti-stress activity is calculated by the equation $$A = \left(1 - \frac{TS - V}{VS - V}\right) \times 100$$

Where V is the vehicle, TS and VS is the drug and vehicle treated groups of animals, respectively.

ADVANTAGES

1. The present invention provides a bioactive composition having enhanced hepatoprotective, immunostimulant and antistress properties.
2. The present invention discloses a process for the preparation of synergistic composition constituting three compounds used as markers.

3. The three marker compounds belong to the class of iridoid compounds viz., acetyl barlerin and shanzhiside methyl ester.
4. The synergistic bioactive constituent obtained by the process of the present invention does not contain any toxicity.
5. The process of the present invention provides optimal yields of the synergistic fraction from the plant.

What is claimed is:

1. A novel synergistic pharmaceutical composition comprising a bioactive fraction of iridoid glucosides obtained from the plant *Barleria prionitis linn*, said bioactive fraction comprising the following ingredients:
    (a) barlerin in the range of 1.6–6.2%;
    (b) acetyl barlerin in the range of 0.015–0.38%;
    (c) shanshizide methylesters in the range of 4.4–8.0%; and
    (d) pharmaceutically accepted additives, and having hepatoprotective, antistress and immunorestorative properties on subjects.

2. A composition according to claim 1, wherein said composition is used to treat hepatic injury caused by Carbon tetrachloride, Acetaminophen, and Galactosamine.

3. A composition according to claim 2, wherein the prefered dosagefor $CCl_4$ induced hepatotoxicity in mammals is 20–200 mg/kg of body weight.

4. A composition according to claim 2, wherein the hepatoprotective activity in $CCl_4$ induced hepatotoxic mammals is upto 88%.

5. A composition according to claim 2, wherein the dosage for Acetaminophen, induced hepatotoxicity in mammals is in the range of 50–100 mg/kg of body weight.

6. A composition according to claim 2, wherein the hepatoprotective activity in acetaminophen induced hepatotoxicity in mammals is up to 86%.

7. A composition according to claim 2, wherein the dosage for Galactosamine induced hepatotoxicity in mammals is in the range of 50–100 mg/kg of body weight.

8. A composition according to claim 2, wherein the hepatoprotective activity in Galactosamine induced hepatotoxicity in mammals is up to 86%.

9. A composition according to claim 1, wherein the dosage for anti-fatigue activity in mammals is in the range of 25–100 mg/kg of body weight.

10. A composition according to claim 9, wherein the preferred dosage for anti-fatigue activity in mammals is in the range of 50–100 mg/kg of body weight.

11. A composition according to claim 9, wherein the anti-fatigue effect in mammals is over 80%.

12. A composition according to claim 1, wherein the dosage for immunorestorative activity is in the range of 50–100 mg/kg of body weight.

13. A composition according to claim 1, wherein the immunorestorative activity is upto 70%.

14. A composition according to claim 1, wherein said composition reduces the elevated levels of serum glutaminpyruvic transaminase (GPT) by about 92%.

15. A composition according to claim 1, wherein said composition reduces the elevated levels of serum glutamicoxalo acetic transaminase (GOT) by about 74%.

16. A composition according to claim 1, wherein said composition reduces the elevated levels of serum alkaline phosphatase (ALP) by about 88%.

17. A composition according to claim 1, wherein said composition reduces the elevated levels of serum triglycerides by about 88%.

18. A composition according to claim 1, wherein the hepatoprotective activity of said composition against the elevated level of bilirubin is about 85.96%.

19. A composition according to claim 1, wherein the subject is selected from mammals.

20. A composition according to claim 1, wherein said composition is used singly or in combination with pharmaceutically acceptable carriers.

21. A composition according to claim 1, wherein said composition is administered to a subject in combination with a pharmaceutically acceptable additives, carriers, diluents, solvents, filters, lubricants, excipients, binder or stabilizers.

22. A composition according to claim 1, wherein the desired dosage is administered for both preventive and curative properties.

23. A composition according to claim 1, wherein said composition is administered systemically, orally or by any clinically/medically accepted methods.

24. A composition according to claim 1, wherein the subject is selected from animals.

25. A composition according to claim 1, wherein the preferred dosage for human beings is about 10–15 mg/kg of body weight.

26. A process for the after preparation of synergistic bioactive constituent composition according to claim 1 comprising iridoid glucosides (a) acetyl barlerin (b) barlerin (c) shanzhiside methyl ester, said process comprising the steps of:
    (a) extracting the powdered plant material with aqueous alcohol;
    (b) concentrating the extract under reduced pressure at a temperature upto 45° C.;
    (c) partitioning the concentrate between water and a moderately polar organic solvent; and
    (d) evaporating the aqueous constituent at a temperature upto 45° C. to complete dryness to yield the bioactive constituent.

27. A process according to claim 26, wherein the aqueous alcohol is selected from the group consisting of ethanol, methanol and a mixture thereof.

28. A process according to claim 26, wherein the aqueous ethanol and aqueous methanol is in the range of 3:7 to 1:9.

29. A process according to claim 26, wherein the organic solvent used for partitioning is selected from the group consisting of chloroform, dichloromethene, diethyl ether, methylene chloride and/or ethyl acetate.

30. A process according to claim 26, wherein the plant material is selected from the aerial parts consisting of leaves, stems and bark or mixture thereof.

31. A process according to claim 26, wherein the extract containing the bioactive constituent is either evaporated in a freeze drier or using a thin film evaporator.

32. A method of treating subjects with hepatotoxicity, immunodeficiency and stress, said method comprising administering a pharmaceutically effective dosage of synergistic composition of bioactive fraction comprising iridoid glucosides from the plant source extracted from *Barleria prionitis linn*, to the selected subjects, said composition comprising:
    (a) barlerin 1.6–6.2%;
    (b) acetyl barlerin 0.015–0.38%; and
    (c) shanshizide methylesters 4.4–8.0%.

33. A method according to claim 32, wherein said composition is used to treat hepatic injury caused by Carbon tetrachloride, Acetaminophen, and Galactosamine.

34. A method according to claim 32, wherein the dosage for $CCl_4$ induced hepatotoxicity in mammals is in the range of 20–200 mg/kg of body weight.

35. A method according to claim 32, wherein the hepatoprotective activity in CCl$_4$ induced hepatotoxic mammals is upto 88%.

36. A method according to claim 32, wherein the dosage for Acetaminophen induced hepatotoxicity in mammals is in the range of 50–100 mg/kg of body weight.

37. A method according to claim 32, wherein the hepatoprotective activity in acetaminophen induced hepatotoxicity in mammals is up to 86%.

38. A method according to claim 32, wherein the dosage for Galactosamine induced hepatotoxicity in mammals is in the range of 50–100 mg/kg of body weight.

39. A method according to claim 32, wherein the hepatoprotective activity in Galactosamine induced hepatotoxicity in mammals is up to 86%.

40. A method according to claim 32, wherein the dosage for anti-fatigue activity in mammals is in the range of 50–100 mg/kg of body weight.

41. A method according to claim 32, wherein the anti-fatigue effect in mammals is over 80%.

42. A method according to claim 32, wherein the dosage for immunorestorative activity is in the range of 50–100 mg/kg of body weight.

43. A method according to claim 32, wherein the immunorestorative activity is upto 70%.

44. A method of treating a subject with the composition of claim 1 to reduce the elevated levels of serum glutaminpyruvic transaminase (GPT) by about 92%.

45. A method of treating a subject with the composition of claim 1 to reduce the elevated levels of serum glutamic-oxalo acetic transaminase (GOT) by about 74%.

46. A method of treating a subject with the composition of claim 1 to reduce the elevated levels of serum alkaline phosphatase (ALP) by about 88%.

47. A method of treating a subject with the composition of claim 1 to reduce the elevated levels of serum triglycerides by about 88%.

48. A method according to claim 32, wherein the hepatoprotective activity of said composition against the elevated level of bilirubin is about 85.96%.

49. A method of treating a subject with the composition of claim 1 having apathological condition selected from stomach or liver disorder.

50. A method according to claim 32, wherein the subject is selected from mammals.

51. A method according to claim 32, wherein said composition is used singly or in combination with pharmaceutically acceptable carriers.

52. A method according to claim 32, wherein said composition is administered to a subject in combination with a pharmaceutically acceptable additives, carriers, diluents, solvents, filters, lubricants, excipients, binder or stabilizers.

53. A method according to claim 32, wherein the desired dosage is administered for both preventive and curative properties.

54. A method according to claim 32, wherein said composition is administered systemically and orally.

55. A method according to claim 32, wherein the subject is selected from animals.

56. A method as claimed in claim 32, wherein the preferred dosage for human beings is about 10–15 mg/kg of body weight.

57. A composition according to claim 19, wherein the subject is a human.

58. A composition according to claim 24, wherein the animal is a mammal.

59. A composition according to claim 24, wherein the animal is a human.

60. The method of claim 50 wherein the mammal subject is a human.

61. The method of claim 55, wherein the animal subject is a mammal.

62. The method of claim 55, wherein the animal subject is a human.

* * * * *